United States Patent [19]

Claeson et al.

[11] Patent Number: 4,537,896
[45] Date of Patent: Aug. 27, 1985

[54] THROMBIN INHIBITING ARYLSULFONYL GUANIDINOPHENYLALANINE AMIDES

[75] Inventors: Carl G. Claeson, Lidingö; Stig I. Gustavsson, Mölndal, both of Sweden

[73] Assignee: KabiVitrum AB, Stockholm, Sweden

[21] Appl. No.: 504,338

[22] Filed: Jun. 14, 1983

[30] Foreign Application Priority Data

Jun. 23, 1982 [SE] Sweden ................................ 8203887

[51] Int. Cl.$^3$ .................. A61K 31/445; A61K 31/16; C07D 211/16; C07C 147/13

[52] U.S. Cl. .................................... 514/330; 514/211; 514/212; 514/218; 514/229; 514/255; 514/423; 514/602; 514/603; 260/239 B; 260/239 BC; 260/330.6; 544/162; 544/391; 546/206; 546/226; 548/540; 564/84; 564/91; 564/86

[58] Field of Search .......... 260/239 B, 239 BC, 330.6; 544/162, 391; 546/206, 226; 548/540; 564/84, 91, 86; 424/248.5, 250, 267, 274, 321

[56] References Cited

U.S. PATENT DOCUMENTS

| 3,884,896 | 5/1975 | Blomback et al. | 260/112.5 |
| 3,978,045 | 8/1976 | Okamoto et al. | 260/239 B |
| 4,069,323 | 1/1978 | Okamoto et al. | 424/244 |

FOREIGN PATENT DOCUMENTS

| 2655636 | 6/1977 | Fed. Rep. of Germany . |
| 2726392 | 12/1977 | Fed. Rep. of Germany . |
| 2290193 | 6/1976 | France . |
| 1516668 | 7/1978 | United Kingdom . |
| 1538206 | 1/1979 | United Kingdom . |

OTHER PUBLICATIONS

Kikumoto et al., "Thrombin Indicators", J. Med. Chem., (1980), 23, pp. 830–836.
Klausner et al., "The Interaction of α-N-(-p-Toluenesulphonyl)-p-Guanidino-L-Phenylalanine Methyl Ester with Thrombin and Trypsin", Biochem. J., (1978), 169, pp. 157–167.
Sturzebecher, J. et al., "Synthetische Inhibitoren der Serin proteinasen", Pharmazie, 36, H. 9, (1981), pp. 639–641.
Hauptmann, J. et al., "Anticoagulant and Antithrombotic Action of Novel Specific Inhibitors of Thrombin", Thromb. Haem., 43, (1980), pp. 118–123.
Elliot, D. et al., "Bacteriostasis in the Amino Acid Series", J. Chem. Soc., (1949), pp. 1374–1378.
Tsunematsu, H. et al., "Interactions of Derivatives of Guanidinophenylglycine and Guanidinophenylalanine with Trypsin and Related Enzymes, J. Biochem., 88, (1980), pp. 1773–1783.
Shinji Tonomura et al., Kobe J. Med. Sci., 26, 1–9, Mar. 1980, "A Novel Series of Synthetic Thrombin-Inhibitors".
Thrombosis Research, 29; 635–642, 1983, Pergamon Press Ltd., "Cyclic Amides of N-α-Arylsulfonyl-Aminoacylated 4-Amino-Phenylalanine-Tight Binding Inhibitors of Thrombin", J. Sturzebecher et al.
Moore, S. et al., "Synthesis of Analogues of Bradykinin with Replacement of the Arginine Residues by 4-Guanidinophenyl-L-alanine, J. Chem. Soc. Perkin I, (1977), pp. 2025–2030.
Blomback et al., Chemistry and Biology of Thrombin Ann Arbor Science Pub., Ann Arbor, Michigan, (1977) pp. 276–290.

Primary Examiner—Henry R. Jiles
Assistant Examiner—Dale A. Bjorkman
Attorney, Agent, or Firm—Pollock, Vande Sande & Priddy

[57] ABSTRACT

New thrombin inhibiting N$^\alpha$-arylsulfonyl-p-guanidinophenylalanine amides of the formula

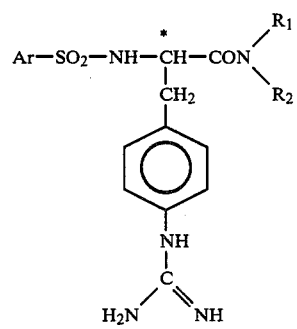

wherein Ar is a substituted aryl and $R_1$ and $R_2$ are an alkyl group having 1-5 carbon atoms or together with the amine nitrogen form an heterocyclic ring, in racemate form as well as in form of optical active antipodes, theirs pharmaceutically acceptable salts, methods for their preparation, pharmaceutical composition and diagnostical preparation containing these compounds, use of the compounds in treatments of thrombosis and methods of treatment of thrombosis as well as methods for determination of thrombin concentration in blood.

14 Claims, No Drawings

THROMBIN INHIBITING ARYLSULFONYL GUANIDINOPHENYLALANINE AMIDES

TECHNICAL FIELD

The present invention is related to new thrombin inhibiting $N^\alpha$-arysulfonyl-p-guanidinophenylalanine amides of the general formula:

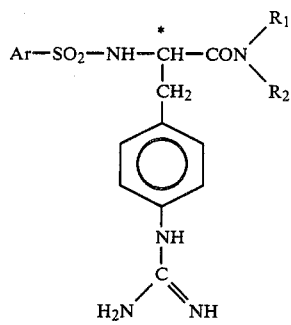

wherein Ar is o-, m- or p-tolyl, naphthyl-1, naphthyl-2 or 5-dimethylamino-1-naphthyl and $R_1$ and $R_2$ is an alkyl group having 1–5 carbon atoms or

is a ring system

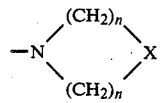

wherein n=2 or 3 and
X is a single bond, $CH_2$, $CH-CH_3$, $CH-C_2H_5$, $CH-C_3H_5$, O, NH or $N-CH_3$.

BACKGROUND ART

Thrombin plays an important role in the coagulation process, where it as last enzyme, in the coagulation cascade, transfer fibrinogen to polymerizable fibrin. This is done by splitting of Arg-bonds. Thrombin has just close to its active center a "specificity pocket" with great affinity for the positively charged guanidion group in Arg. This knowledge has been used for construction of synthetic substrates and inhibitors of thrombin. Since a long time it is known that substituted Arg esters can be split by thrombin, e.g. Bz-Arg-OEt (BAEE) and Tos-Arg-OMe (TAME). The last-named ester acts, by being a competitive substrate, also as inhibitor to the reaction of thrombin with fibrinogen. The plasma coagulation time is prolonged e.g. by addition of TAME.

A better thrombin inhibitor can be obtained by making the Arg-bond not cleavable. Okamoto[1,2] has described thrombin inhibitors, where the carboxylic group of Arg is bound to sec amines:

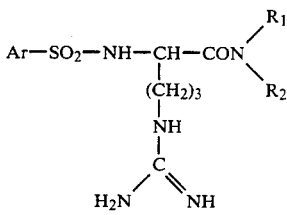

Markwardt[3,4] has modified the structure II by inserting the synthetic amino acid p-amidinophenylalanine (Aph), an analog to Arg, instead of Arg. The compounds (III) thereby obtained seem to be about as good thrombin inhibitors as the corresponding compounds (II) made by Okamoto.

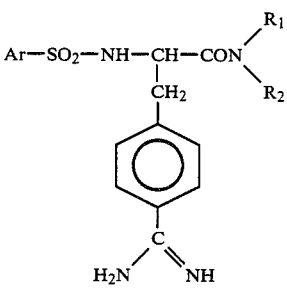

Another arginine anolog, p-guanidinophenylalanine (Gph), was first synthezised by Elliot[5]. Klausner[6] synthesized the derivative Tos-Gph-OMe, which appeared to be a good substrate for trypsin, but on the other hand a bad substrate for thrombin but with ability to inhibit the amidase- and esterase activity of thrombin. Tsunematso[7] has synthesized Bz-Gph-OEt too and has found that it as substrate for trypsin is comparable with Tos-Gph-OMe and Tos-Arg-OMe (TAME).

DESCRIPTION OF THE INVENTION

Now we have found that the new compounds (I) according to the invention have very good thrombin inhibiting properties which to advantage can be compared with the corresponding Arg- as well as Aph-derivatives (II and III). Table 1 compares Gph- and Arg-derivatives with respect to the inhibition constant (Ki) for thrombin and prolongation of coagulation time initiated by thrombin (thrombin time). Especially the thrombin times show the advantages of the Gph-derivates. Table 2 gives Ki (thrombin) for the corresponding Gph- and Aph-derivatives. Also in this comparison the Gph-derivatives show a distinct advantage.

The new prepared compounds according to the invention have a very specific thrombin inhibiting effect. For example factor Xa is inhibited up to 1000 times less than thrombin. The compounds are therefor very useful as selective inhibitors for thrombin when determining factor Xa in a medium (e.g. blood), where thrombin may be present and disturb the determination of factor Xa. Besides this diagnostic use of the new compounds as thrombin inhibitors they are also useful for a direct specific determinator of thrombin in blood.

The new aryl-sulfonyl-L-p-guanidinophenylalanine amides and the pharmaceutically acceptable acid addition salts thereof according to the invention can in their capacity as good thrombin inhibitors also be used as anticoagulants in therapy and prophylaxis of thrombosis.

In the synthesis of the new thrombin inhibitors, protecting groups and coupling methods traditionally well-known in chemistry can be used. The C-terminal amide residues are also coupled using methods of synthesis which are well-known in the organic chemistry. Purifying of intermediates and end products is made by precipitation, crystallization or gel filtration chromatography.

Thus the compounds according to the invention can be prepared by (a) reaction between a compound of the formula

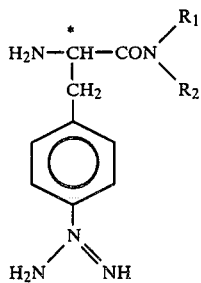

wherein $R_1$ and $R_2$ are as defined previously, and a compound of the formula Ar—SO$_2$—Y wherein Y is a reactive group, e.g. halogen as Cl which together with H$_2$N can form a sulfonamide group and where Ar is as defined previously.

(b) by removal of the NO$_2$-group e.g. by hydrogenation in a compound of the formula

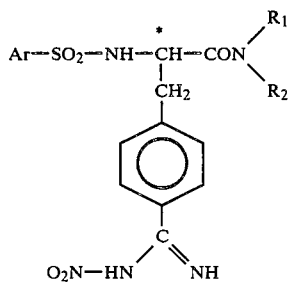

wherein $R_1$, $R_2$ and Ar are as defined previously.

The starting material according to (a) above can be obtained by removal of the protecting group Z from a compound of the formula

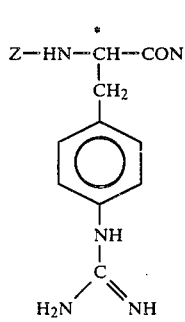

by reaction with e.g. trifluoroacetic acid, wherein $R_1$ and $R_2$ are as defined previously and Z is a removable group as —COOR°, wherein R° is a hydrocarbon residue e.g. alkyl.

The starting material according to (b) above can be obtained by e.g. a reaction between a compound of the formula

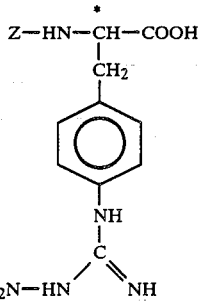

and a compound of formula

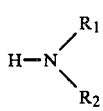

wherein Z, $R_1$ and $R_2$ are as defined previously, to formation of a compound of the formula

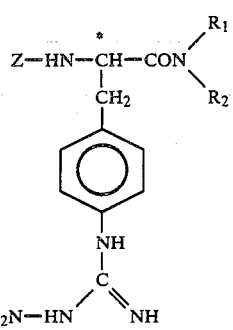

which protecting group Z thereafter is removed to formation of a compound

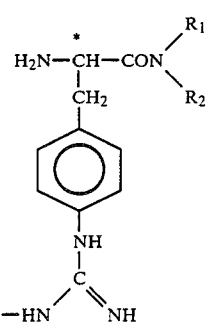

which thereafter by reaction with a compound of the formula

Ar—SO$_2$—Y wherein $R_1$, $R_2$, Y and Z are as defined previously, is transferred to the starting material according to (b).

The new compounds according to the invention show a asymmetric center (*) and appear therefore in two stereoisomeric forms as well as in form of racemate. The two optical antipodes can be separated with help of known methods and the invention includes the racemate as well as these antipodes separately as free base as well as salt. Specially preferred is the L-form.

Many different organic and inorganic acids can be employed to form acid addition salts of the new $N^\alpha$-arylsulfonyl-guanidinophenyl-alanine amides of this invention. The product of the reactions described above can be isolated in free form or as acid addition salts. In addition, the product can be obtained as pharmaceutically acceptable acid addition salts by reacting one of the free bases with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like. Similarly, a treatment of the acid addition salts by reaction of a base gives as result a reformation of the free amide or ester.

The invention is described from the following not limiting examples.

Abbreviations

Arg=L-Arginine
Phe=L-Phenylalanine
Aph=p-Amidino-Phe
Gph=p-Guanidino-L-Phe
Dansyl=5-Dimethylamino-1-naphthalenesulfonyl
Bz=Benzoyl
Et=Ethyl
Me=Methyl
BOC=t-Butyloxycarbonyl
Ac=Acetyl
DCCI=Dicyclohexylcarbodiimide
DCU=Dicyclohexylurea
DMF=Dimethylformamide
HOBT=N-Hydroxybenzotriazole
TFA=Trifluoroacetic acid
TLC=Thin Layer Chromatography Used methods for Thin Layer Chromatography At TLC-analysis pre-fabricated glass plates, with silica gel $F_{254}$ (Merck) as an absorption medium, are used. The solvent systems used are (volume ratios):

A: n-Butanol:AcOH:$H_2O$ (3:2:1)
$Pa_6$: Chloroform:MeOH:AcOH:$H_2O$ (34:4:9:2)

Following chromatography, the plate is inspected in UV light (254 nm) and then developed with chlorine/o-tuluidin reagent according to normal procedure. The given $R_f$ values are the result of single experiments.

EXAMPLE 1

$N^\alpha$-Dansyl-p-guanidino-Phe-piperidide hydrochloride (1a) BOC-p-(nitroguanidino)-Phe-piperidide 1.3 g of BOC-p-(nitroguanidino)-Phe-OH (Moore S. et al. J. Chem. Soc. Perkin I 1977, 2025–30) in 15 ml of DMF is cooled to $-15°$ C. 0.5 ml of $Et_3N$ and then 0.5 ml isobutylchloroformiate is added with stirring. After 15 min. 0.4 ml of piperidine is added and the solution is stirred at continued cooling for 1 hour and then further 1 hour at room temperature. The reaction mixture is evaporated in vacuum to an oil which is triturated with water and dried. The residue is dissolved in methanol and chromatographed on a Sephadex ® LH20 column in methanol with methanol as medium for eluation. The fraction containing the compound 1a is evaporated to dryness in vaccum, the product is obtained as an amorphous powder.

Yield: 0.95 g (62%) of compound 1a
TLC: $R_f=0.79$ ($Pa_6$)

(1b) $N^\alpha$-Dansyl-p-(nitroguanidino)Phe-piperidide 1,5 g of Ia is suspended in a 25% solution of TFA in dichloromethane and is stirred at room temperature for 30 min. Dichloromethane is evaporated. The residue is cooled on an ice-bath and ca 1000 ml dry ether is added under vigorous stirring. The precipitate formed is filtered and washed with dry ether and dried in vacuum over NaOH. The obtained TFA salt of H-p-(nitroguanidino)-Phe-piperidide is dissolved in 20 ml tetrahydrofurane-water (9:1) and neutralized at a low temperature (about $-10°$ C.) of 0.55 ml of $ET_3N$. 1.2 g of dansylchloride and further 0.6 ml of $Et_3N$ is added. The solution is stirred for 2 hours at a low temperature and then at room temperature over night. The precipitated product is filtered and washed carefully with water and thereafter with ether.

Yield: 1.8 g (92%) of compound 1b
TLC: $R_f=0.84$ ($Pa_6$)

1. $N^\alpha$-Dansyl-p-guanidino-Phe-piperidide hydrochloride 200 mg of Ib is suspended in 10 ml of methanol and 0.07 ml of conc. HCl and 20 mg palladium on carbon (10%) are added. The solution is hydrogenated at room temperature and at atmospheric pressure for 48 h. The catalyst is filtered off and the reaction mixture is evaporated. The residue is dissolved in 5 ml of methanol and chromotographed on Sephadex ® LH20 in methanol with methanol as medium for eluation. The fraction containing compound 1 is evaporated. The residue is dissolved in 5 ml ethanol:water (1:1) and is ion-exchanged on QAE Sephadex ® A25 in chloride form in ethanol:water (1:1) with the same medium for eluation. The fraction containing the pure compound 1 is evaporated and the residue is lyophilized from water.

Yield: 150 mg (71%) of compound 1.
TLC: $R_f=0.43$ (A) shows one spot. Data of analysis vide table 3.

EXAMPLE 2

$N^\alpha$-(Naphthalene-2-sulfonyl)-p-guanidino-Phe-4-methyl-piperidide hydrochloride (2a)
BOC-p-guanidino-Phe-4-methyl-piperidine hydrochloride 1.1 g of 4-methylpiperidide in 20 ml of DMF is acidified with 1 ml of conc. HCl and is then evaporated to dryness in vacuum. The residue together with 3.2 g of BOC-p-guanidino-Phe-OH [Klausner Y.S. et al. Biochem. J. 169, 157–67 (1978)] and 1.35 g of HOBT are dissolved in 20 ml DMF. After cooling in an ice bath 2.5 g of DCCI is added. The reaction mixture is stirred for 2 hours at a low temperature and then at room temperature over night. The prepared DCU is filtered off and the reaction mixture is evaporated in vacuum to an oil. The oil is dissolved in 80 ml of n-butanol. The butanol solution is washed in sequence with 10% NaCl in water, 0.5 M $NaHCO_3$ in 5% NaCl in water and 10% NaCl in water. The butanol phase is dried over $Na_2SO_4$ and evaporated in vacuum. Chromoatography on Sephandex ® LH20 in methanol and on QAE Sephadex ® A50 in chloride form in ethanol-water (1:1) gives after lyophilizing from water a pure compound 2a.
Yield: 3.0 g (68%) of compound 2a.
TLC: $R_f$=0.64 ($Pa_6$).

2. $N^\alpha$-(Naphthalene-2-sulfonyl)-p-guanidino-Phe-4-methyl-piperidide hydrochloride 1.3 g of compound 2a is deprotected with 30 ml of 25% TFA in dichloromethane according to 1b. The TFA salt of H-p-guandino-Phe-4-methyl-piperidide is dissolved in 25 ml of DMF and after cooling 0.42 mg of $Et_3N$ is added to give a weak basic reaction. First 3.3 g of naphthalene-2-sulfonylchoride and then 0.45 ml of $Et_3N$ are added to the solution. The reaction mixture is stirred for 1 hour at a low temperature and for 1 hour at room temperature. After cooling $Et_3N$ hydrochloride is filtered off and the DMF-solution is evaporated in vacuum. Chromatography and lyophilizing according to ex. 1 gives a pure compound 2.
Yield: 1.24 g (79%) of compound 2.
TLC: $R_f$=0.51 (A) shows one spot.
Data of analysis vide table 3.

Determination of thrombin inhibition

Data and test results of other synthesized aryl-p-guanidinophenylalanine amides are compared in table 3, where compound V is prepared according to ex. 1 and the other compounds are prepared according to ex. 2.

Determination of Ki

The inhibition of reaction of the enzymes (human thrombin; Sigma Chemical Co., St. Louis, U.S.A. and human factor Xa; KabiVitrum AB, Stockholm) with the substrates (S-2238 resp. S-2222, Kabi Diagnostica, Stockholm) was determined at three different substrate concentrations from 0.3 to 2 km. Six different inhibitor concentrations, which give inhibition from 40% to 90%, were incubated with the enzyme for 30 seconds at 37° C. The buffer composition, ionic strength, pH and enzyme concentration were the same as those recommended in the booklets from Kabi Diagnostica. The initial reaction velocity ($\Delta A$/min) was measured on a recorder at 405 nm. Ki values were than graphically determined from Dixon and Lineweaver-Burk diagrams.

Thrombin time

A volume of 200 µl citrate-plasma was heated for 1 minute at 37° C. The coagulation was started by adding 10 µl fresh thrombin solution (about 5 NIH U/ml) and the coagulation time was registrated by a fibrinometer. At the inhibition experiments the plasma was incubated for 30 seconds with 10 µl inhibitor solution at different concentrations before the thrombin solutions was added.

TABLE 1

| Compound | No | Ki (thrombin) | Thrombin time plasma | Thrombin time fibrinogen |
|---|---|---|---|---|
| Tos—Arg—piperidide | | $5.10^{-6}$ | $3,5.10^{-5}$ | $4.10^{-4}$ |
| Tos—Gph—piperidide | v | $8.10^{-7}$ | $1.10^{-6}$ | $8.10^{-6}$ |
| Dansyl—Arg—piperidide | | $9.10^{-8}$ | $2.10^{-6}$ | $2.10^{-6}$ |
| Dansyl—Gph—piperidide | i | $9.10^{-8}$ | $6.10^{-7}$ | $6.10^{-7}$ |
| Tos—Gph—OMe | | $7,5.10^{-6}$ | $8,3.10^{-5}$ | |

Thrombin inhibition by Arg- and Gph-derivatives

Ki of thrombin in mol/l.

"Thrombin time" designates the concentration (mol/l) of the inhibitor, which doubles the thrombin time of dog plasma. The Arg derivates have been synthesized according to ref. 1 and 2.Tos-Gph-OMe has been synthesized according to ref. 6.

TABLE 2

| Compound | No | Ki (thrombin) |
|---|---|---|
| Tos—Aph—piperidide | | $2,3.10^{-6}$ |
| Tos—Gph—piperidide | v | $8.10^{-7}$ |
| α-Naphthalenesulfonyl—Aph—4-methylpiperidide | | $1,8.10^{-6}$ |
| α-Naphthalenesulfonyl—Gph—4-methylpiperidide | iii | $3,5.10^{-7}$ |
| β-Naphthalenesulfonyl—Aph—4-methylpiperidide | | $1,1.10^{-6}$ |
| β-Naphthalenesulfonyl—Gph—4-methylpiperidide | ii | $3,1.10^{-7}$ |
| β-Naphthalenesulfonyl—Aph—morpholide | | $3,1.10^{-6}$ |
| β-Naphthalenesulfonyl—Gph—morpholide | iv | $1,8.10^{-7}$ |

Thrombin inhibition constants of Aph- and Gph-derivate

Ki of thrombin is given in mol/l.
Ki-values of Aph-derivatives are taken from ref. 3. They refer to the racemates of the compounds and are determined by bovine thrombin and DL-benzoylarginine-p-nitroanilide.

TABLE 3

Compound

Ar—SO₂—Gph—N(R₁)(R₂)

—N(R₁)(R₂)

| No | ArSO₂— | R₂ | $R_f$(A) | $[\alpha]_D^{25}$ C = 0.5 50% AcOH | Elemental analysis Upper: Found Lower: Calculated C | H | N | Cl |
|---|---|---|---|---|---|---|---|---|
| i | 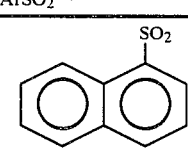 | 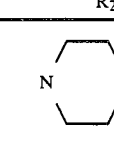 | 0,43 | +117° | 57,2 58,0 | 6,0 6,3 | 14,7 15,0 | 6,5 6,3 |

TABLE 3-continued

| | Ar-SO₂- | -N(R₁)(R₂) | Ki (mol/l) | "Thrombin time" | | | | |
|---|---|---|---|---|---|---|---|---|
| ii | 2-naphthyl-SO₂ | 4-methylpiperidine ×HCl | 0,51 | +82°,7 | 58,4 / 58,9 | 5,8 / 6,1 | 12,9 / 13,2 | 6,5 / 6,7 |
| iii | 1-naphthyl-SO₂ | 4-methylpiperidine ×HCl | 0,51 | +103° | 58,9 / 58,9 | 5,8 / 6,1 | 13,1 / 13,2 | 7,0 / 6,7 |
| iv | 2-naphthyl-SO₂ | morpholine ×HCl | 0,39 | +66°,0 | 55,6 / 55,6 | 5,6 / 5,5 | 13,4 / 13,5 | 6,8 / 6,8 |
| v | 4-methylphenyl-SO₂ | piperidine ×HCl | 0,45 | +78°,1 | 55,1 / 55,0 | 6,0 / 6,3 | 14,5 / 14,6 | 7,2 / 7,4 |
| vi | 1-naphthyl-SO₂ (5-N(CH₃)₂) | hexamethyleneimine ×HCl | 0,46 | +100° | 58,0 / 58,7 | 6,8 / 6,5 | 14,4 / 14,7 | 6,4 / 6,2 |
| vii | 1-naphthyl-SO₂ (5-N(CH₃)₂) | 4-propylpiperidine ×HCl | 0,53 | +135° | 59,0 / 59,9 | 7,0 / 6,9 | 13,8 / 14,0 | 6,1 / 5,9 |
| viii | 1-naphthyl-SO₂ (5-N(CH₃)₂) | 4-methylpiperazine ×2HCl | 0,11 | +14°,8 | 53,4 / 53,1 | 6,3 / 6,1 | 16,0 / 16,1 | 11,7 / 11,6 |
| ix | 1-naphthyl-SO₂ (5-N(CH₃)₂) | N(CH₃)(C₄H₉) ×HCl | 0,48 | +98°,4 | 57,6 / 57,8 | 6,9 / 6,7 | 14,7 / 15,0 | 6,5 / 6,3 |

Compound

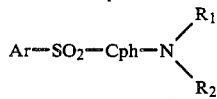

Ar—SO₂—Cph—N(R₁)(R₂)

Ki (mol/l)    "Thrombin time"

TABLE 3-continued
| No | ArSO$_2$— | —N$\begin{smallmatrix}R_1\\R_2\end{smallmatrix}$ | Thrombin | FXa | Concentration (mol/l) required to prolong the coagulation time by a factor of 2 |
|---|---|---|---|---|---|
| i | 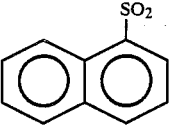 |  | $9.10^{-8}$ | $2,5.10^{-4}$ | $6.10^{-7}$ |
| ii | 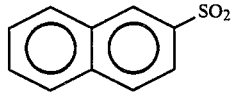 | 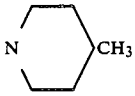 | $3,1.10^{-7}$ | $2.10^{-5}$ | $1.10^{-6}$ |
| iii | 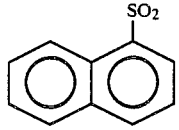 | 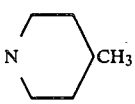 | $3,5.10^{-7}$ | $3,7.10^{-4}$ | $6,7.10^{-6}$ |
| iv | 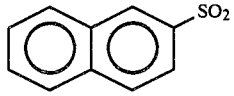 |  | $1,8.10^{-7}$ | $5.10^{-5}$ | $8.10^{-7}$ |
| v | 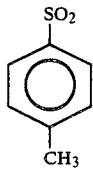 |  | $8.10^{-7}$ | $2,5.10^{-4}$ | $1.10^{-6}$ |
| vi | 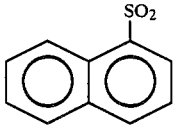 | 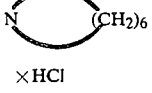 | $8.10^{-8}$ | $3.10^{-4}$ | $1,6.10^{-7}$ |
| vii | 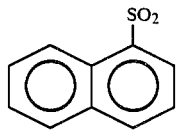 | 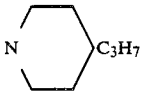 | $2,3.10^{-7}$ | $2.10^{-4}$ | $1.5.10^{-5}$ |
| viii | 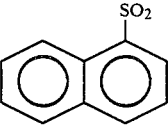 | 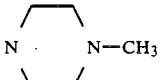 | $7.10^{-7}$ | $3.10^{-4}$ | $1.6.10^{-7}$ |

TABLE 3-continued

| ix | 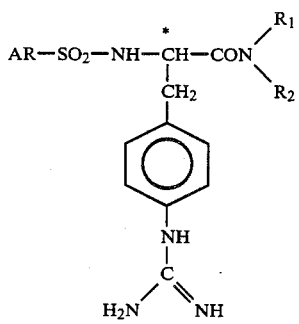 | 3,5.10$^{-7}$ | 1,3.10$^{-4}$ | 2.5.10$^{-7}$ |

REFERENCES

1. Okamoto, S., et al. SE patent appl. No. 760891-5
2. Okamoto, S., et al. J. Med. Chem. 23, 830–836 (1980)
3. Stürzenbecher, J., et al. Pharmazie 36, 639–641 (1981)
4. Hauptmann, J., Thromb. Haem. 43, 118–123 (1980)
5. Elliot, D. F., och Harrington, C., J. Chem. Soc. 1949, 1374–1378
6. Klausner, Y. S., et al. Biochem. J. 169, 157–167 (1978)
7. Tsunematsu, H., et al. J. Biochem. 88, 1773–1783 (1980)
8. Moore, S., el al. J. Chem. Soc. Perkin I, 1977, 2025–2030.

We claim:

1. N$^\alpha$-arylsulfonyl-p-guanidinophenylalanine amides of the formula

AR—SO$_2$—NH—CH—CON$\diagup^{R_1}_{R_2}$
     |
     CH$_2$
     |
     C$_6$H$_4$
     |
     NH
     |
     C(=NH)NH$_2$    I wherein Ar is ortho-, meta- or para-tolyl, naphthyl-1, naphthyl-2 or 5-dimethylamino-1-naphthyl; R$_1$ and R$_2$ are an alkyl group having 1–5 carbon atoms or

is a ring system

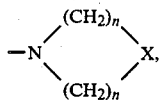

wherein n=2 or 3 and X is a single-bond, CH$_2$, CH—CH$_3$, CH—CH$_2$H$_5$, CH—CH$_3$H$_7$, O, NH or N—CH$_3$, in free base form or in form of pharmaceutically acceptable acid addition salt thereof.

2. A compound according to claim 1, wherein Ar is 5-dimethyl-1-naphthyl an

is piperidyl residue.

3. A compound according to claim 1 in hydrochloride form.

4. A compound according to claim 2 in hydrochloride form.

5. A compound according to claim 1 in racemate form.

6. A compound according to claim 2 in racemate form.

7. A compound according to claim 1 in form of its optical antipodes.

8. A compound according to claim 2 in form of its optical antipodes.

9. A compound according to claim 1 in substantially pure L-form.

10. A compound according to claim 2 in substantially pure L-form.

11. Pharmaceutical composition for treatment or prevention of thrombosis containing one or more compounds according to claim 1 in an amount effective for said treatment or said prevention and a carrier.

12. Pharmaceutical composition for treatment or prevention of thrombosis containing one or more compounds according to claim 2 in an amount effective for said treatment or said prevention and a carrier.

13. A method of treatment or prevention of thrombosis, characterized in that to a host in need of such treatment is administrated a therapeutically effective amount of at least one compound according to claim 1.

14. A method of treatment or prevention of thrombosis, characterized in that to a host in need of such treatment is administrated a therapeutically effective amount of at least one compound according to claim 2.

* * * * *

UNITED STATES PATENT AND TRADEMARK OFFICE
CERTIFICATE OF CORRECTION

PATENT NO. : 4,537,896

DATED : August 27, 1985

INVENTOR(S) : Claeson, et al.

It is certified that error appears in the above—identified patent and that said Letters Patent is hereby corrected as shown below:

Column 14, Claim 2, line 18, change "an" to --- and ---.

Column 1, line 53, change "guanidion" to --- guanidino ---.

Signed and Sealed this

Thirty-first Day of December 1985

[SEAL]

Attest:

DONALD J. QUIGG

Attesting Officer

Commissioner of Patents and Trademarks